US00PP17365P3

(12) United States Plant Patent
Heuger

(10) Patent No.: US PP17,365 P3
(45) Date of Patent: Jan. 16, 2007

(54) ***BEGONIA* PLANT NAMED 'BBVOLVIR'**

(50) Latin Name: *Begonia×hybrida*
Varietal Denomination: Bbvolvir

(75) Inventor: Josef Heuger, Glandorf (DE)

(73) Assignee: Begonia Breeders Assoc. B.V., Aalsmeer (NL)

( * ) Notice: Subject to any disclaimer, the term of this patent is extended or adjusted under 35 U.S.C. 154(b) by 0 days.

(21) Appl. No.: 11/141,521

(22) Filed: May 31, 2005

(65) Prior Publication Data

US 2005/0223459 P1 Oct. 6, 2005

(51) Int. Cl.
*A01H 5/00* (2006.01)

(52) U.S. Cl. ..... Plt./346
(58) Field of Classification Search ..... Plt./346
See application file for complete search history.

(56) References Cited

PUBLICATIONS

Upov Plant Database Variety UPOV–ROM 2006/01 search for cultivar BBVOLVIR.*

* cited by examiner

*Primary Examiner*—Kent Bell
*Assistant Examiner*—Annette H Para
(74) *Attorney, Agent, or Firm*—C. A. Whealy

(57) ABSTRACT

A new and distinct cultivar of *Begonia* plant named 'Bbvolvir', characterized by its compact, upright and mounded plant habit; freely flowering habit; double flowers with yellow-colored tepals; and excellent flower longevity.

1 Drawing Sheet

Botanical designation: *Begonia×hybrida.*
Cultivar denomination: 'Bbvolvir'.

CROSS-REFERENCE TO RELATED APPLICATIONS

*Begonia* Plant Named 'Bbvolbro'; Josef Heuger, Applicant.

*Begonia* Plant Named 'Bbvolkra'; Josef Heuger, Applicant.

BACKGROUND OF THE INVENTION

The present Invention relates to a new and distinct cultivar of *Begonia* plant, botanically known as *Begonia×hiemalis,* commercially known as Elatior *Begonia,* and hereinafter referred to by the name 'Bbvolvir'.

The new *Begonia* was discovered and selected by the Inventor in a controlled environment in Glandorf, Germany in May, 2000, as a naturally-occurring whole plant mutation of the *Begonia×hiemalis* cultivar Genie, disclosed in U.S. Plant Pat. No. 12,886. The new *Begonia* was observed as a single plant in a group of flowering plants of the parent selection.

Asexual reproduction of the new *Begonia* by cuttings in a controlled environment in Glandorf, Germany since 2001, has shown that the unique features of this new *Begonia* are stable and reproduced true to type in successive generations.

SUMMARY OF THE INVENTION

The cultivar 'Bbvolvir' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bbvolvir'. These characteristics in combination distinguish 'Bbvolvir' as a new and distinct *Begonia:*

1. Compact, upright and mounded plant habit.
2. Freely flowering habit.
3. Double flowers with yellow-colored tepals.
4. Excellent flower longevity.

Plants of the new *Begonia* can be compared to plants of the parent, the cultivar Genie. In side-by-side comparisons conducted in Glandorf, Germany, plants of the new *Begonia* differed from plants of the cultivar Genie in the following characteristics:

1. Plants of the new *Begonia* had smaller cymes than plants of the cultivar Genie.
2. Plants of the new *Begonia* and the cultivar Genie differed in tepal coloration as plants of the cultivar Genie had light salmon red and yellow bi-colored tepals.
3. Plants of the new *Begonia* and the cultivar Genie differed in pedicel and flower bract coloration as plants of the cultivar Genie had yellow orange-colored pedicels and flower bracts.

Plants of the new *Begonia* can be compared to plants of the cultivar Bbvolbro, disclosed in a U.S. Plant patent application Ser. No. 11/114,524, and the cultivar Bbvolkra, disclosed in a U.S. Plant patent application Ser. No. 11/114, 523. In side-by-side comparisons conducted in Glandorf, Germany, plants of the new *Begonia* differed from plants of the cultivars Bbvolbro and Bbvolkra primarily in tepal coloration.

Plants of the new *Begonia* can also be compared to plants of the cultivar 00/3, disclosed in U.S. Plant Pat. No. 13,208. In side-by-side comparisons conducted in Glandorf, Germany, plants of the new *Begonia* differed primarily from plants of the cultivar 00/3 in tepal coloration as plants of the cultivar 00/3 had orange red and yellow bi-colored tepals.

BRIEF DESCRIPTION OF THE PHOTOGRAPH

The accompanying colored photograph illustrates the overall appearance of the new *Begonia,* showing the colors as true as it is reasonably possible to obtain in colored reproductions of this type. Colors in the photograph may differ slightly from the color values cited in the detailed botanical description which accurately describe the colors of the new *Begonia.* The photograph comprises a side perspective view of a typical flowering plant of 'Bbvolvir' grown in a container.

DETAILED BOTANICAL DESCRIPTION

In the following description, color references are made to The Royal Horticultural Society Colour Chart, 1995 Edition, except where general terms of ordinary dictionary significance are used. The aforementioned photograph and following observations and measurements describe plants grown in Aalsmeer, The Netherlands during the spring and summer under conditions typical of commercial practice in a glass-covered greenhouse. During the production of the plants, day and night temperatures ranged from 15 to 20° C. and light levels were about 18,000 lux. Plants used for the photograph and the description were grown in 13-cm containers and were about three months old when the photograph and description were taken.

Botanical classification: *Begonia×hiemalis* cultivar Bbvolvir.

Commercial classification: Elatior *Begonia.*

Parentage: Naturally-occurring whole plant mutation of the *Begonia×hiemalis* cultivar Genie, disclosed in U.S. Plant Pat. No. 12,886.

Propagation:

*Type.*—By cuttings.

*Time to initiate roots.*—About two weeks at temperatures of 20° C.

*Time to produce a rooted young plant.*—About 20 to 35 days at temperatures of 20° C.

*Root description.*—Fine, fibrous and freely branched. Plants of the new *Begonia* have not been observed to form tubers.

Plant description:

*Plant form and habit.*—Compact, upright and mounded plant habit; freely branching with about five to six basal branches per plant. Moderately vigorous. Vegetative shoots are formed at basal nodes and flowering shoots are formed at upper nodes.

*Plant height.*—About 20 cm.

*Plant width.*—About 20 to 25 cm.

*Lateral branches.*—Length: About 8 to 13 cm. Diameter: About 1 to 3 cm. Texture: Smooth, glabrous. Color: 144B.

*Leaves.*—Arrangement: Alternate, simple. Length: About 7 cm. Width: About 5 to 6 cm. Shape: Roughly ovate; asymmetrical. Apex: Acute. Base: Cordate. Margin: Doubly crenate. Texture, upper and lower surfaces: Smooth, glabrous; velvety. Venation pattern: Palmate. Color: Developing leaves, upper surface: 136A. Developing leaves, lower surface: 139A. Fully expanded leaves, upper and lower surfaces: 136B. Venation, upper and lower surfaces: 136B. Petiole length: About 4 to 6 cm. Petiole diameter: About 4 mm. Petiole texture, upper and lower surfaces: Smooth, glabrous. Petiole color, upper and lower surfaces: 136B. Stipule quantity: One to two per leaf. Stipule size: About 1 cm by 1 cm. Stipule texture, upper and lower surfaces: Smooth, glabrous. Stipule color, upper and lower surfaces: Close to 136A.

Flower description:

*Flowering habit.*—Double flowers with about 10 to 15 tepals per flower; flowers arranged in axillary cymes; about five to six open flowers per cyme; numerous cymes in flower simultaneously; about 25 to 30 open flowers per plant. Flowers positioned above and beyond the foliage and face upright to outwardly. Flowers not fragrant.

*Natural flowering season.*—Under natural daylight conditions, plants flower from spring until the fall. Flower initiation and development is induced by long day/short night conditions. Flowering continuous under photoinductive conditions.

*Flower longevity.*—Individual flowers last about four to five weeks on the plant; flowers persistent.

*Cyme height.*—About 4 to 5 cm.

*Cyme diameter.*—About 5 to 7 cm.

*Flowers.*—Shape: Oval to rounded; double. Diameter: About 4 to 5 cm. Depth (height): About 1 cm.

*Flower buds.*—Length: About 1 to 1.5 cm. Diameter: About 2 cm. Shape: Ovoid. Color: Close to 1D.

*Tepals.*—Arrangement: Rosette. Shape: Obovate to rounded. Apex: Rounded. Base: Obtuse. Margin: Entire to slightly crenate. Length: About 2 to 3 cm. Width: About 3 to 4 cm. Texture, upper and lower surfaces: Smooth, glabrous; satiny. Color: When opening, upper surface: 2C. When opening, lower surface: 1D. Fully opened, upper surface: 6D; towards the margins, close to 43A; color becoming closer to 10D with development. Fully opened, lower surface: 4D.

*Flower bracts.*—Quantity: Two per flower. Arrangement: Opposite. Length: About 1 cm. Width: About 1 cm. Shape: Broadly cordate. Apex: Acute. Base: Cuneate. Margin: Entire. Texture, upper and lower surfaces: Smooth, glabrous. Color, upper surface: 6D. Color, lower surface: 4D.

*Peduncles.*—Angle: About 30 to 45° from vertical. Length: About 4 to 5 cm. Diameter: About 3 to 4 mm. Strength: Strong. Texture: Smooth, glabrous. Color: 144B.

*Pedicels.*—Angle: About 30 to 45° from vertical. Length: About 2 to 3 cm. Diameter: About 1 to 3 cm. Strength: Strong. Texture: Smooth, glabrous. Color: 13B.

*Reproductive organs.*—Stamens: None observed. Pistils: None observed.

*Seed/fruit.*—Seed and fruit production has not been observed as reproductive organs are not formed.

Disease/pest resistance: Plants of the new *Begonia* have not been observed to be resistant to pathogens and pests common to *Begonia.*

It is claimed:

1. A new and distinct cultivar of *Begonia* plant named 'Bbvolvir', as illustrated and described.

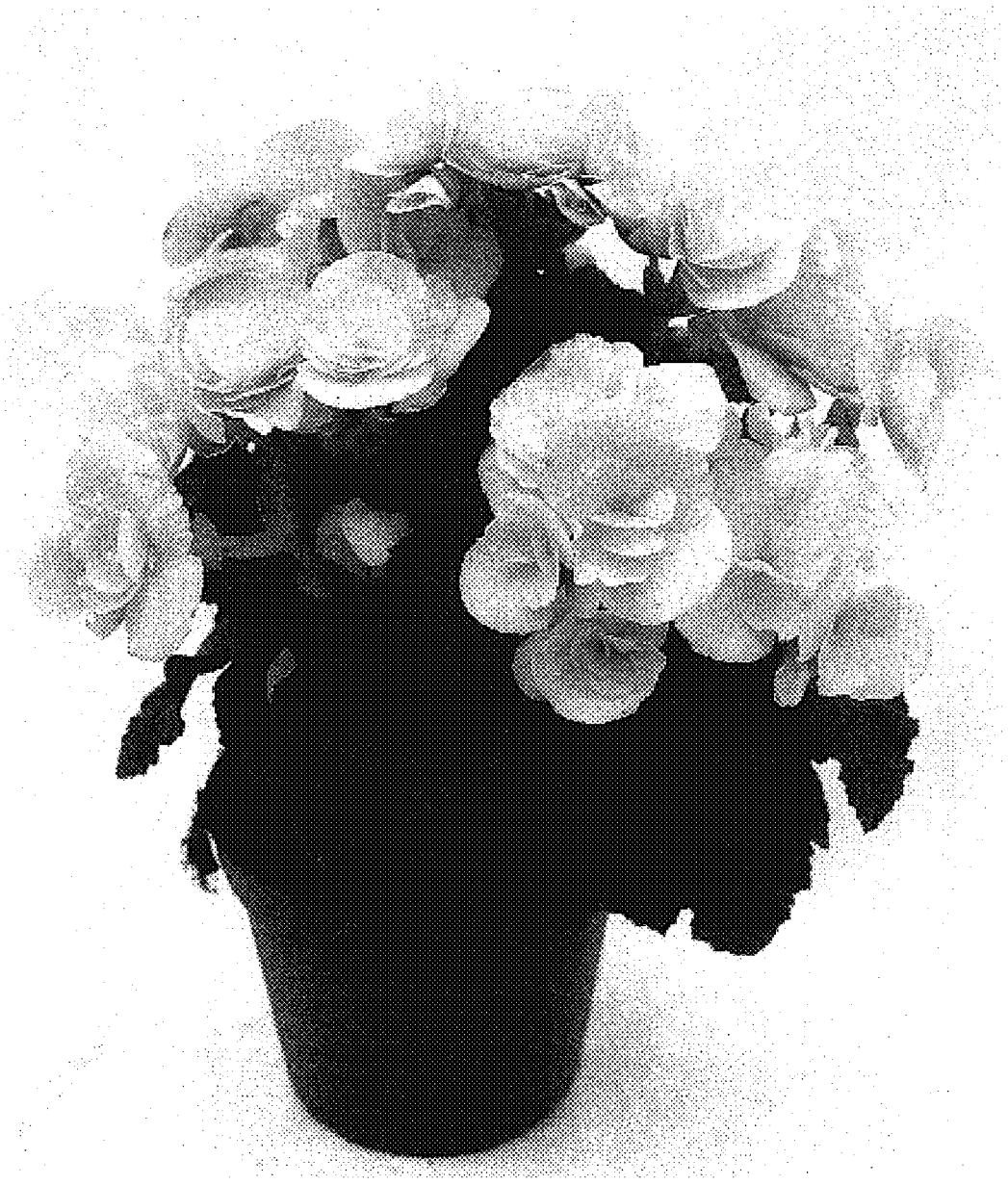

* * * * *